US00PP13013P2

(12) United States Plant Patent
de Gruyter

(10) Patent No.: US PP13,013 P2
(45) Date of Patent: Sep. 24, 2002

(54) CODIAEUM PLANT NAMED 'GRU CO9901'

(75) Inventor: André Paulus de Gruyter, Rockanje (NL)

(73) Assignee: Vulcan Plants Produktonwikkeling B.V., Rockanje (NL)

( * ) Notice: Subject to any disclaimer, the term of this patent is extended or adjusted under 35 U.S.C. 154(b) by 2 days.

(21) Appl. No.: 09/801,594

(22) Filed: Mar. 9, 2001

(51) Int. Cl.[7] ..... A01H 5/00
(52) U.S. Cl. ..... Plt./373
(58) Field of Search ..... Plt./373

(56) References Cited

PUBLICATIONS

UPOV ROM GTITM Computer Database, GTI JOVE Retrival software, 2001/06, citation for 'Wilma'.*

* cited by examiner

*Primary Examiner*—Bruce R. Campell
*Assistant Examiner*—W C Baker
(74) *Attorney, Agent, or Firm*—C. A. Whealy

(57) ABSTRACT

A distinct cultivar of Codiaeum plant named 'GRU CO9901', characterized by its upright and compact growth habit; uniquely-colored green, yellow and dark pink variegated leaves that do not fade during the winter; thick and strong leaves; and excellent post-production longevity.

1 Drawing Sheet

BACKGROUND OF THE INVENTION

The present invention relates to a new and distinct cultivar of Codiaeum plant, botanically known as *Codiaeum variegatum*, and hereinafter referred to by the name 'GRU CO9901'.

The new Codiaeum originated from a cross made by the Inventor in 1992, in Rockanje, The Netherlands, of the *Codiaeum variegatum* cultivar Petra, not patented, as the female, or seed, parent with the *Codiaeum variegatum* cultivar Iceton, not patented, as the male, or pollen, parent. The new Codiaeum was discovered and selected by the Inventor as a single plant within the progeny of the stated cross in a controlled environment in Rockanje, The Netherlands. The selection of this plant was based on its unique leaf coloration.

Asexual propagation of the new cultivar at Rockanje, The Netherlands, by terminal cuttings has shown that the unique features of this new Codiaeum plant are stable and reproduced true to type in successive generations of asexual propagation.

SUMMARY OF THE INVENTION

The new Codiaeum has not been observed under all possible environmental conditions. The phenotype may vary somewhat with variations in environment such as temperature and light intensity, without, however, any variance in genotype.

The following traits have been repeatedly observed and are determined to be the unique characteristics of 'GRU CO9901'. These characteristics in combination distinguish 'GRU CO9901' as a new and distinct cultivar:

1. Upright and compact growth habit.
2. Uniquely-colored green, yellow and dark pink variegated leaves that do not fade during the winter.
3. Thick and strong leaves.
4. Excellent post-production longevity.

Plants of the new Codiaeum can be compared to plants of the parent cultivars. In side-by-side comparisons conducted by the Inventor in Rockanje, The Netherlands, plants of the new Codiaeum differed from plants of the parent cultivars Petra and Iceton in the following characteristics:

1. Plants of the new Codiaeum have thicker and stronger leaves than plants of the cultivars Petra and Iceton.
2. Plants of the new Codiaeum and the cultivars Petra and Iceton differ in leaf coloration.
3. Leaves of plants of the cultivars Petra and Iceton fade during the winter whereas leaves of plants of the new Codiaeum do not fade during the winter.

DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Codiaeum. The photograph comprises a side perspective view of a four-month old typical potted plant of 'GRU CO9901'.

DETAILED BOTANICAL DESCRIPTION

The following observations, measurements and comparisons describe plants grown in Rockanje, The Netherlands, in a glass-covered greenhouse with day temperatures about 21 to 27° C. and night temperatures about 20 to 22° C. Plants were about four months from planting and were grown in 17-cm containers. In this description, color references are made to The Royal Horticultural Society Colour Chart except where general terms of ordinary dictionary significance are used.

Botanical classification: *Codiaeum variegatum* cultivar GRU CO9901.

Parentage:

*Female or seed parent.*—*Codiaeum variegatum* cultivar Petra, not patented.

*Male or pollen parent.*—*Codiaeum variegatum* cultivar Iceton, not patented.

Propagation:

*Method.*—By terminal cuttings.

*Time to initiate roots.*—Summer: About 28 days at 26 to 28° C. Winter: About 35 days at 26 to 28° C.

*Time to produce a rooted plant.*—Summer: About 42 days at 26 to 28° C. Winter: About 56 days at 26 to 28° C.

*Root description.*—Thick.

Plant description:

*Plant shape.*—Upright plant habit with upright and outwardly arching leaves; symmetrical. Plants are typically grown as single-stem plants and not pinched.

*Usage.*—Appropriate for 12 to 17-cm containers; indoor plant.

*Plant height from soil level to top of leaf plane.*—About 40 cm.

*Plant diameter or spread.*—About 25 to 35 cm.

*Vertical growth rate.*—About 1.5 to 2.5 cm per week.

*Stem color.*—Towards base of plant, 137B; mid-plant, 200B; towards apex of plant, 137C.

*Internode length.*—About 0.5 to 3 cm.

*Stem texture.*—Smooth, glabrous.

*Foliage description.*—Arrangement: Single; alternate. Length: About 22 to 28 cm. Width: About 9 to 12 cm. Shape: Lanceolate-ovate, lobed. Apex: Cuspidate. Base: Acute. Margin: Entire, undulate. Aspect: Initially upright, then outwardly arching. Thickness: Relatively thick and strong, durable. Texture: Leathery, thick, smooth, glabrous. Venation pattern: Pinnate. Petiole length: About 4 cm. Petiole diameter: About 3 cm. Color: Variegated, glossy on upper surface. Upper surface: Initially green, 137A, veins, 138A. Then, margins and veins, 137A; interveinal, close to 9A. Subsequently, random spots, 61C, develop along veins. Eventually, leaf ground color, 200A to 202A; veins, 187A; and random spots, 52A. Lower surface: Initially 137A to 137C; subsequently, 27A; eventually, 200A with random spots, 52B. Main vein, 139D, lateral veins, 139B. Petiole: 138A.

Flower description: Flowers have not been observed on plants of the new Codiaeum.

Disease resistance: Plants of the new Codiaeum have not been observed to be resistant to pathogens common to Codiaeum.

Postproduction longevity: Plants of the new Codiaeum have been observed to maintain good leaf substance for more than two years in an interior environment.

Temperature tolerance: Plants of the new Codiaeum have been observed to be tolerant to temperatures ranging from 17 to about 35° C.

It is claimed:

1. A new and distinct cultivar of Codiaeum plant named 'GRU CO9901' as illustrated and described.

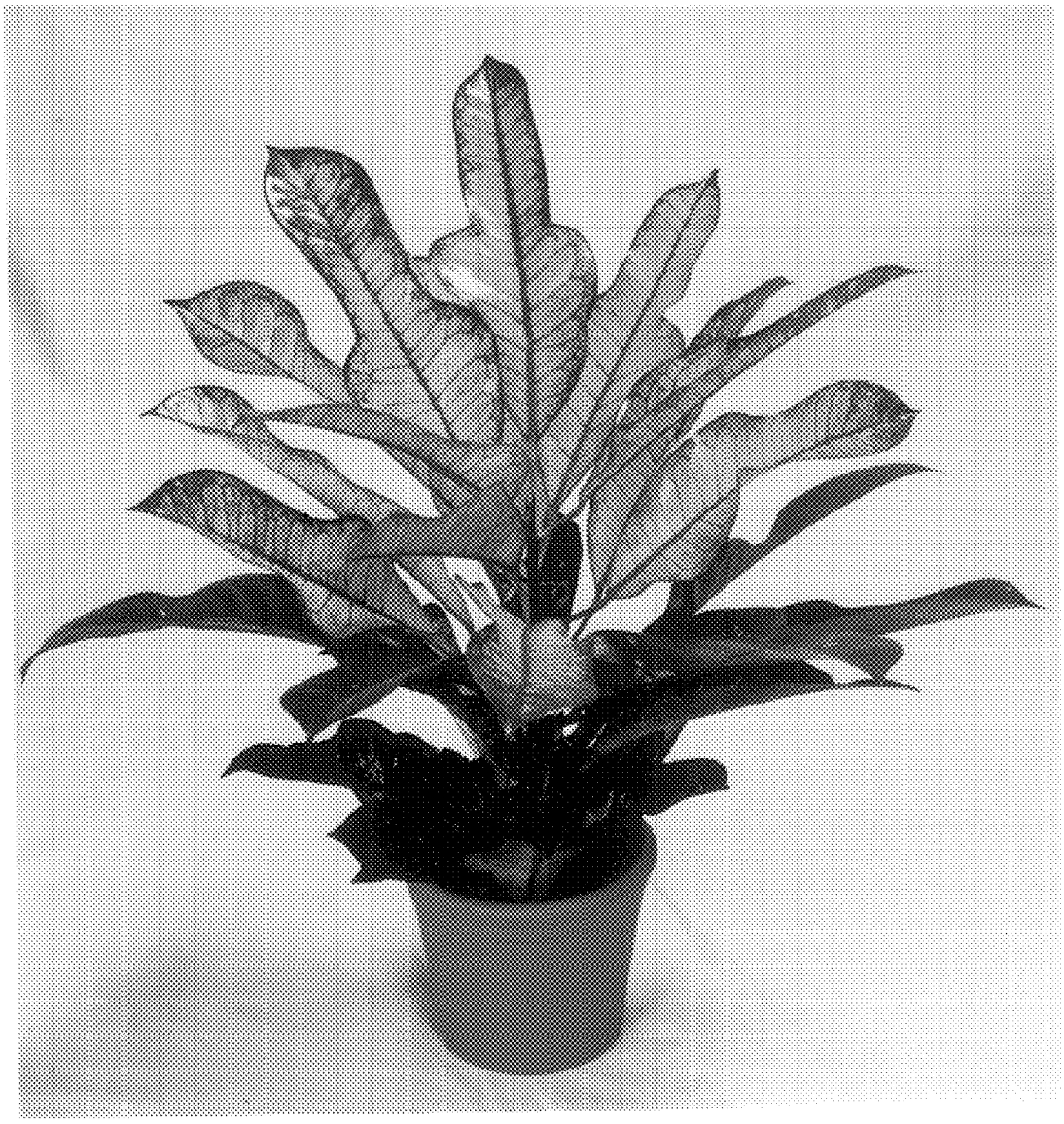

* * * * *